(12) United States Patent
Milella, Jr. et al.

(10) Patent No.: US 11,723,674 B2
(45) Date of Patent: Aug. 15, 2023

(54) DISPOSABLE RASP FOR MEDICAL INSTRUMENTS

(71) Applicant: ECA MEDICAL INSTRUMENTS, INC., Newbury Park, CA (US)

(72) Inventors: Michael J. Milella, Jr., Newbury Park, CA (US); Lauren Thelen, Newbury Park, CA (US); David Tory, Newbury Park, CA (US)

(73) Assignee: ECA Medical Instruments, Inc., Thousand Oaks, CA (US)

( * ) Notice: Subject to any disclaimer, the term of this patent is extended or adjusted under 35 U.S.C. 154(b) by 90 days.

(21) Appl. No.: 17/050,396

(22) PCT Filed: Apr. 23, 2018

(86) PCT No.: PCT/US2018/028956
§ 371 (c)(1),
(2) Date: Oct. 23, 2020

(87) PCT Pub. No.: WO2019/209256
PCT Pub. Date: Oct. 31, 2019

(65) Prior Publication Data
US 2021/0052287 A1   Feb. 25, 2021

(51) Int. Cl.
*A61B 17/16* (2006.01)
*A61B 17/00* (2006.01)

(52) U.S. Cl.
CPC ...... *A61B 17/1659* (2013.01); *A61B 17/1617* (2013.01); *A61B 2017/0023* (2013.01); *A61B 2017/00526* (2013.01)

(58) Field of Classification Search
CPC .................................................. A61B 17/1659
See application file for complete search history.

(56) References Cited

U.S. PATENT DOCUMENTS

| | | | |
|---|---|---|---|
| 3,748,736 A | 7/1973 | Eisen | |
| 4,587,964 A * | 5/1986 | Walker | A61B 17/1659 606/85 |
| 6,120,508 A | 9/2000 | Grunig | |
| 8,679,127 B2 * | 3/2014 | Biegun | A61B 17/154 606/87 |
| 2003/0036764 A1 | 2/2003 | Hamada | |
| 2010/0137922 A1 | 6/2010 | Hunt | |
| 2010/0262146 A1 * | 10/2010 | Tulkis | A61B 17/1659 76/108.1 |
| 2011/0306980 A1 | 12/2011 | Victor | |
| 2016/0045206 A9 | 2/2016 | Stephane | |
| 2016/0262773 A1 | 9/2016 | Edwards | |

OTHER PUBLICATIONS

Extended European Search Report of Application No. 18872657.4 dated Nov. 12, 2021.
European Communication Pursuant to Rule 70(2) and 70a(2) of Application No. 18916571.5 dated Dec. 14, 2021.

* cited by examiner

*Primary Examiner* — Christian A Sevilla
(74) *Attorney, Agent, or Firm* — Ferguson Case Orr Paterson LLP (57) ABSTRACT

Disclosed are aspects of a hybrid plastic and co-molded metal cutting head and a method of forming same. The method includes forming a metal rasp head having a fluid pathway therethrough and molding an elongated body with support into the rasp head via said fluid pathway wherein the fluid pathway into one or more sides.

21 Claims, 12 Drawing Sheets

DISPOSABLE RASP FOR MEDICAL INSTRUMENTS

BACKGROUND

1. Field

This disclosure relates to a plastic disposable mount to withstand forces applied to a shaft supporting a cutting tool.

2. General Background

The medical industry has made use of both reusable and disposable tools and handles. In a surgical context, there is little room for error and the devices must be precise and simple for a surgeon to use during procedures.

Orthopedic surgical procedures can require the creation or enlargement of holes in bones, affixation or removal of fasteners and the like.

Reusable devices require constant recalibration and sterilization to avoid contamination.

DISCLOSURE

Aspects of implementations of devices and methods of a disposable cutting tool with an elongated molded body with a proximal end and a distal end are disclosed herein. Some embodiments according to the present disclosure include a handle portion formed hear the distal end and a support shaft formed near the proximal end, and the support shaft affixed to the rasp head having a height, a top side and a bottom side via portions of the body co-molded into fluid connections within the rasp head.

The tool, in some instances, has a molded neck region extending from the body and formed within the fluid connection. In some instances, a molded collar region is connected to the neck region and formed within a fluid passageway in the rasp head. The passageway extends into sides fluidly connected to the passageway.

The passageway may be one or more of orthogonal and perpendicular to the shaft extending from the top side to the bottom side of the rasp head; at an acute angle to the shaft; at an oblique angle to the shaft; and "Y" shaped extending from the top side to the bottom side of the rasp head.

In some instances, at least one of the rasp head and the support shaft are tapered. In some instances, at least one of the top side and bottom side of the rasp head is parallel to the axis of the rasp head and the other side is angled relative to the axis of the rasp head. In other instances, at least on side is convex or concave.

Disclosed herein are aspects of implementations of devices and methods of an ergonomic disposable rasp with an elongated molded body with a proximal end and a distal end having non-circular regions in cross section on the handle portion, the support shaft affixed to the rasp head having a height, a top side and a bottom side via portions of the body co-molded into fluid connections within the rasp head; and, wherein the non-circular regions provide preselected gripping surfaces on the handle. In some instances, the non-circular regions are at least one of divots, bumps and non-homogeneous generally flat regions.

Also disclosed herein are aspects of implementations of devices and of attaching a rasp head, the method including forming a metal rasp head having a fluid pathway therethrough, then molding an elongated body with a support shaft co-molded into the rasp head via said fluid pathway with the fluid pathway branching into one or more sides. In some instances, the branches are formed at one of an acute and oblique angle to the shaft.

The general description and the following detailed description are exemplary and explanatory only and are not restrictive of the disclosure, as defined in the appended claims. Other aspects of the present disclosure will be apparent to those skilled in the art in view of the detailed description of the disclosure as provided herein.

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale.

FURTHER DISCLOSURE

Rasp tools are an essential part of many surgical procedures. When implanting support devices or replacing bone, a rasp is a commonly used instrument to prepare surfaces for connection. Rasps may also be used to file down bone or alter connecting tissue. Important to any surgery is to minimize contamination, infection and costs.

Figure 1:
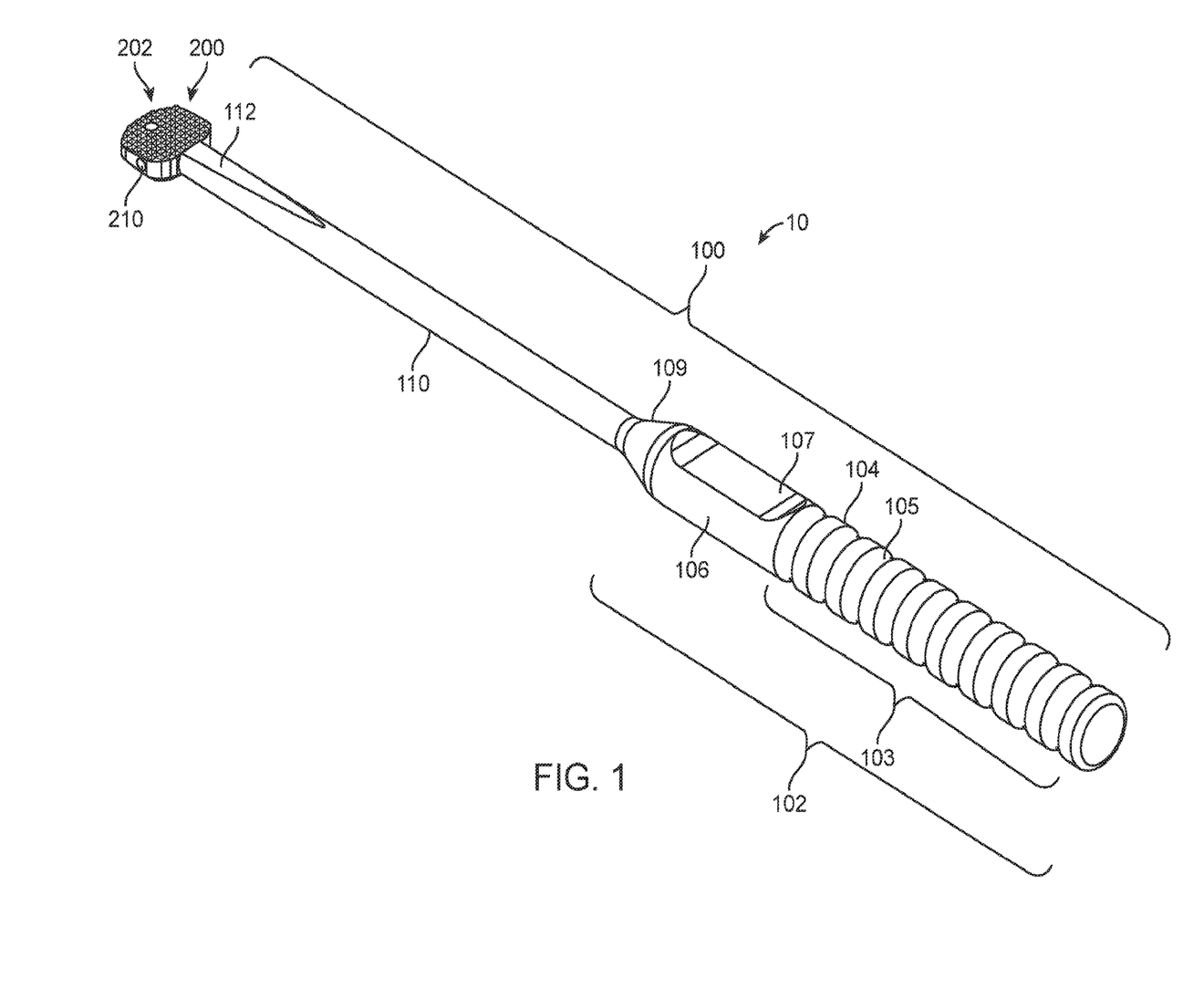
FIGS. 1 and 2 are perspective views of aspects of a hybrid rasp tool.
Figure 2:
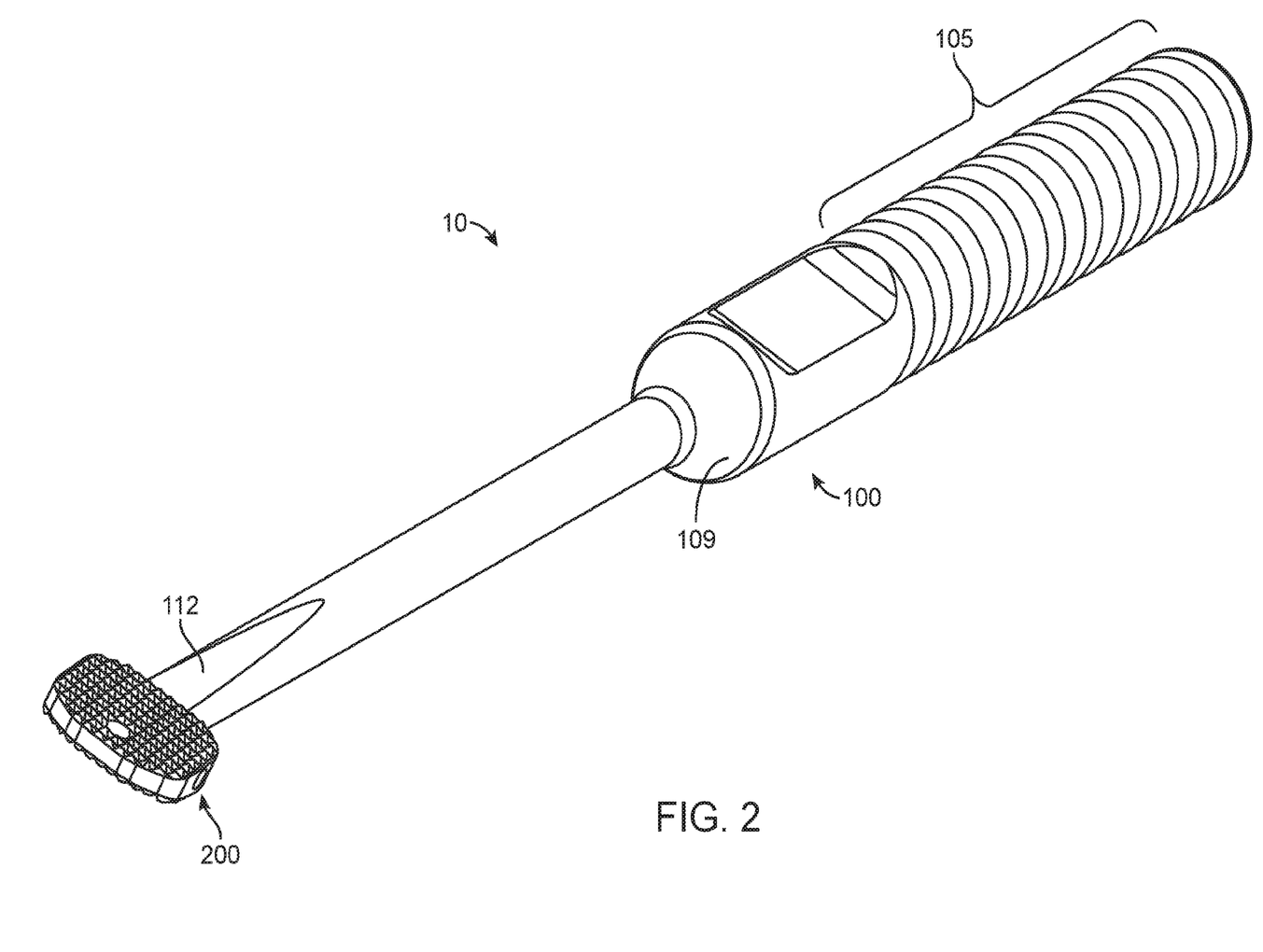

FIGS. 1 and 2 show exterior perspective views of a hybrid rasp tool 10. The body 100 is a plastic injection molded elongated member with a distal end and a proximal end. The handle portion 102 is at one end and the rasp head 200 is at the opposite end. The handle portion may be configured to have varying surface region 103 with features such as bumps 104 or divots 105. The bumps and divots may form ring like geometries covering all or a portion of the varying surface region 103. The varying surface region may be adjacent to a tubular region 106. The tubular region may have one or more non-homogeneous gripping areas 107 such as a flat area configured to press a thumb or finger against during gripping.

The handle portion may taper via a neck 109 to a smaller diameter support shaft 110. In cross section the shaft may be generally circular. In some instances, the portion of the shaft adjacent to the rasp head 200 may be asymmetrically tapered via a tapered region 112 to narrow the shaft to the height of the rasp head 200. The tapered region may be positioned along one or both of the top and bottom faces of the rasp head.

Figure 3A:
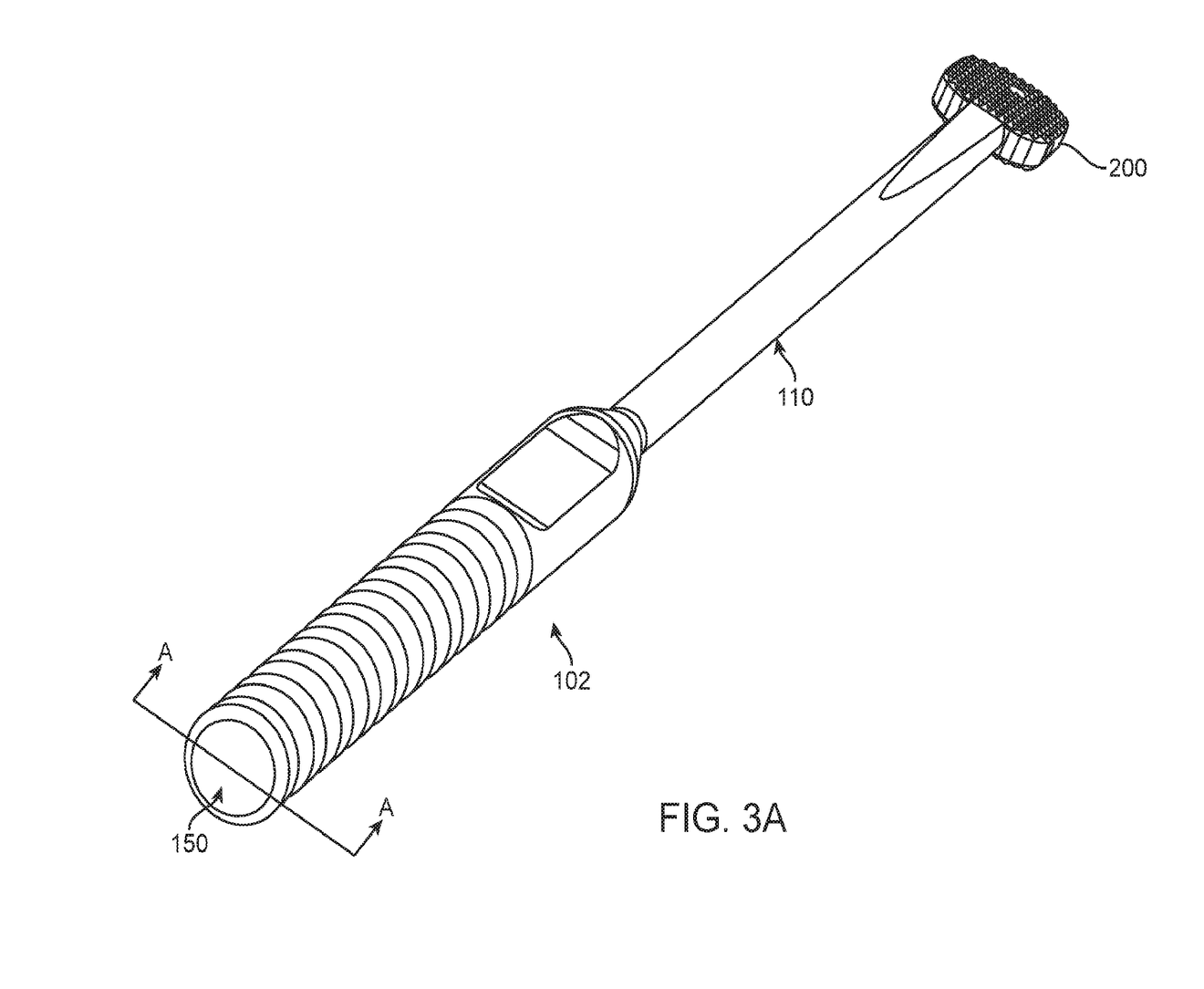
FIGS. 3A-3C show back perspective view, side view and partial side view of a hybrid rasp tool.
Figure 3B:
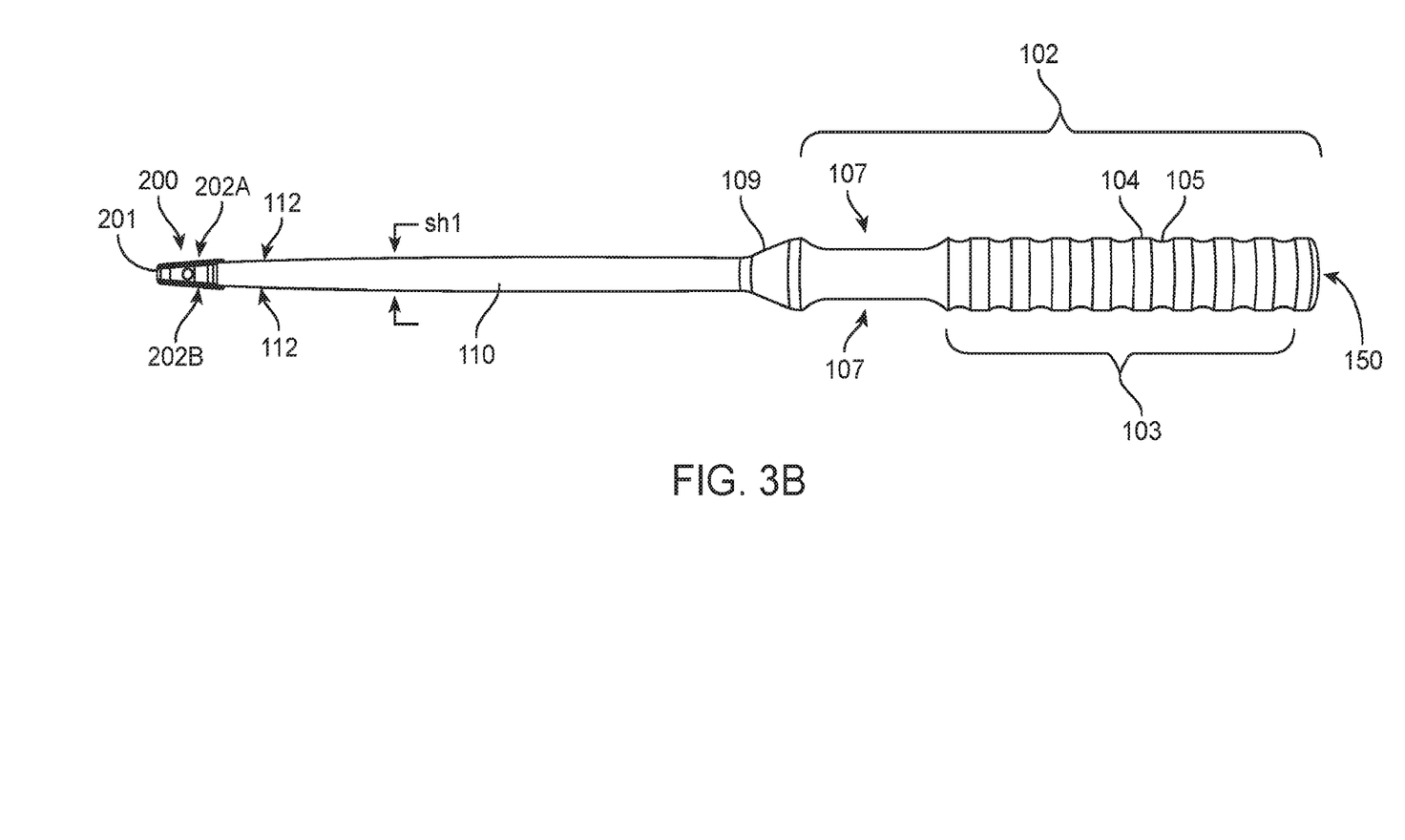
Figure 3C:
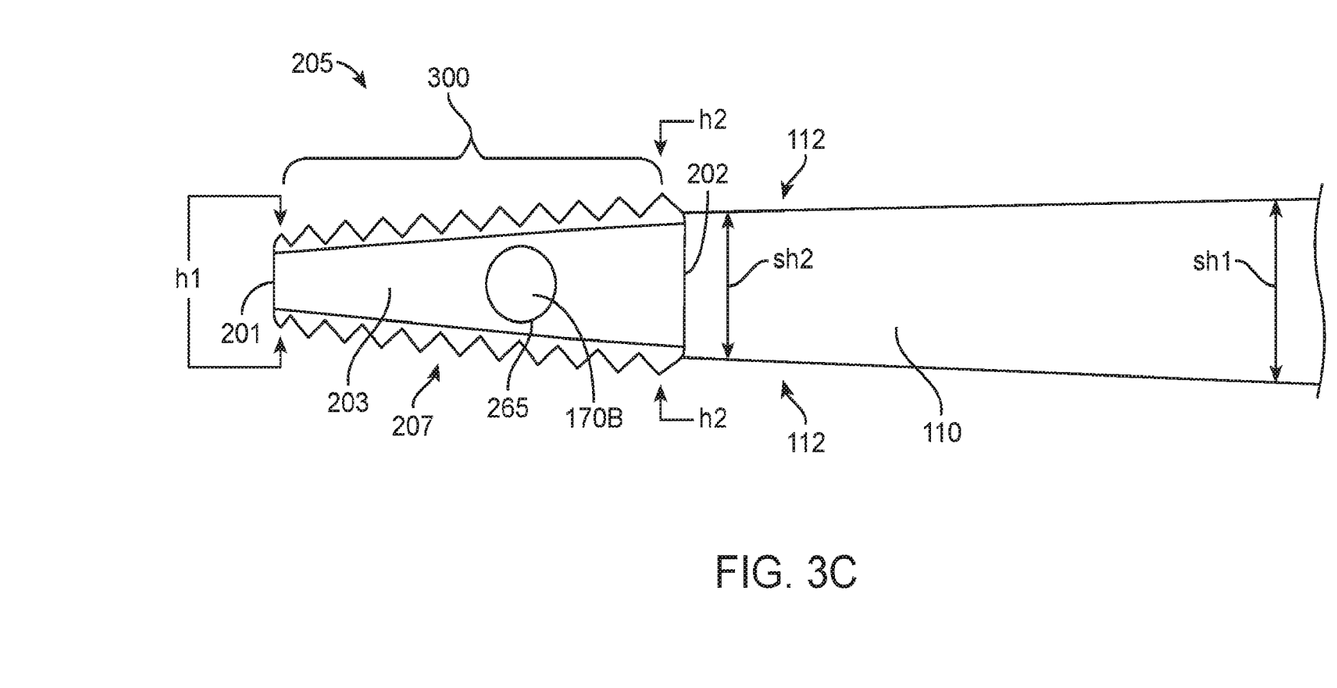
Figure 4:
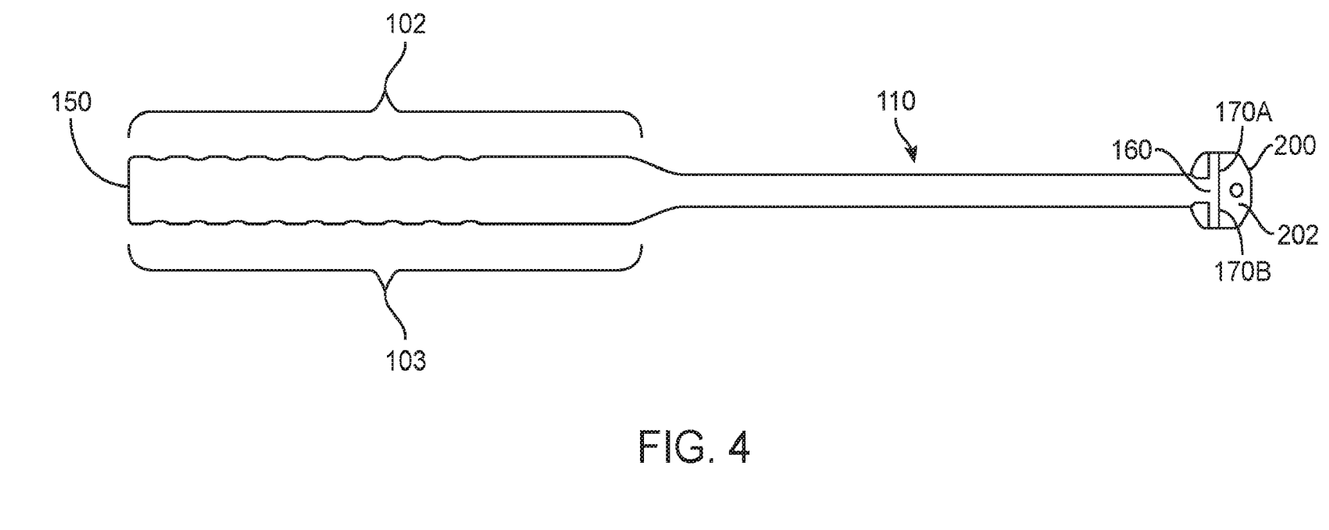
FIG. 4 is a cut-away along the line of A-A in FIG. 3 of a hybrid rasp tool.

FIG. 3A shows a rear perspective view of the rasp tool. FIGS. 3B and 3C show side views of the rasp tool of FIG. 3A. The distal end 150 of the body is visible. FIG. 4 shows a cut-away view of the hybrid rasp of FIG. 3 along the line of "A-A". The body is non-metallic, should be moldable via injection molding, and may be formed of plastics, composites, resins, glass filled plastic or resins and the like.

The rasp body may also have non-homogeneous gripping areas 107 opposite each other. It is important when using a rasp device that the user have a firm grip. During a surgical procedure a surgeon will often have fluids and material on their gloves, and such fluids will act as a lubricant thereby promoting slippage of the hand from a grip. By contouring the body with non-homogeneous gripping areas 107 and bumps and divots, the user's grip may be improved and slippage reduced. A disposable rasp tool allows for the disposal of all medical waste associated with the tool during disposal of the tool. Unlike metal rasp tools, a hybrid rasp tool may be configured to provide flex to assist the user in positioning and using the tool. The rasp head 200 may be configured with concave, convex, flat or tapered top sides and/or bottom sides. The rasp head or heads (in a kit of rasps) may also be formed to mimic the normal lordosis shape of a spine at a predetermined vertebral level. The rasp head or heads (in a kit of rasps) may also be formed to mimic non normal shapes of a spine and thereby selected to match a shape presented by a specific spine. Shown in FIG. 3C is a tapered rasp head with a first height "h1" at the proximal end of the rasp 201 and measured between the top side of the rasp 205 and the bottom side of the rasp 207. The rasp head has a second height "h2" at the distal end of the rasp 202 and measured between the top side of the rasp 205 and the bottom side of the rasp 207. The taper can be seen along the side wall 203 of the rasp head. The shaft 110 may also be tapered from the shaft cross sectional height "sh1" to a non-circular cross sectional height "sh2" forming shaft regions adjacent to the rasp faces generally the same as the rasp head second height. Cutting features 300 of the rasp are shown in a regular pattern on each side of the rasp head. The taper shown on the rasp head and the body is not a limitation. Tapers may vary or be eliminated in some aspects of some embodiments. The rasp is a cutting tool and those of ordinary skill in the art will recognize that drills, scrappers, scalpels, blades and resectors may be connected via the disclosed co-molded process to the handle in lieu of the rasp head and such cutting tools are within the scope of this disclosure. See generally FIGS. 15 through 17.

Figure 5:
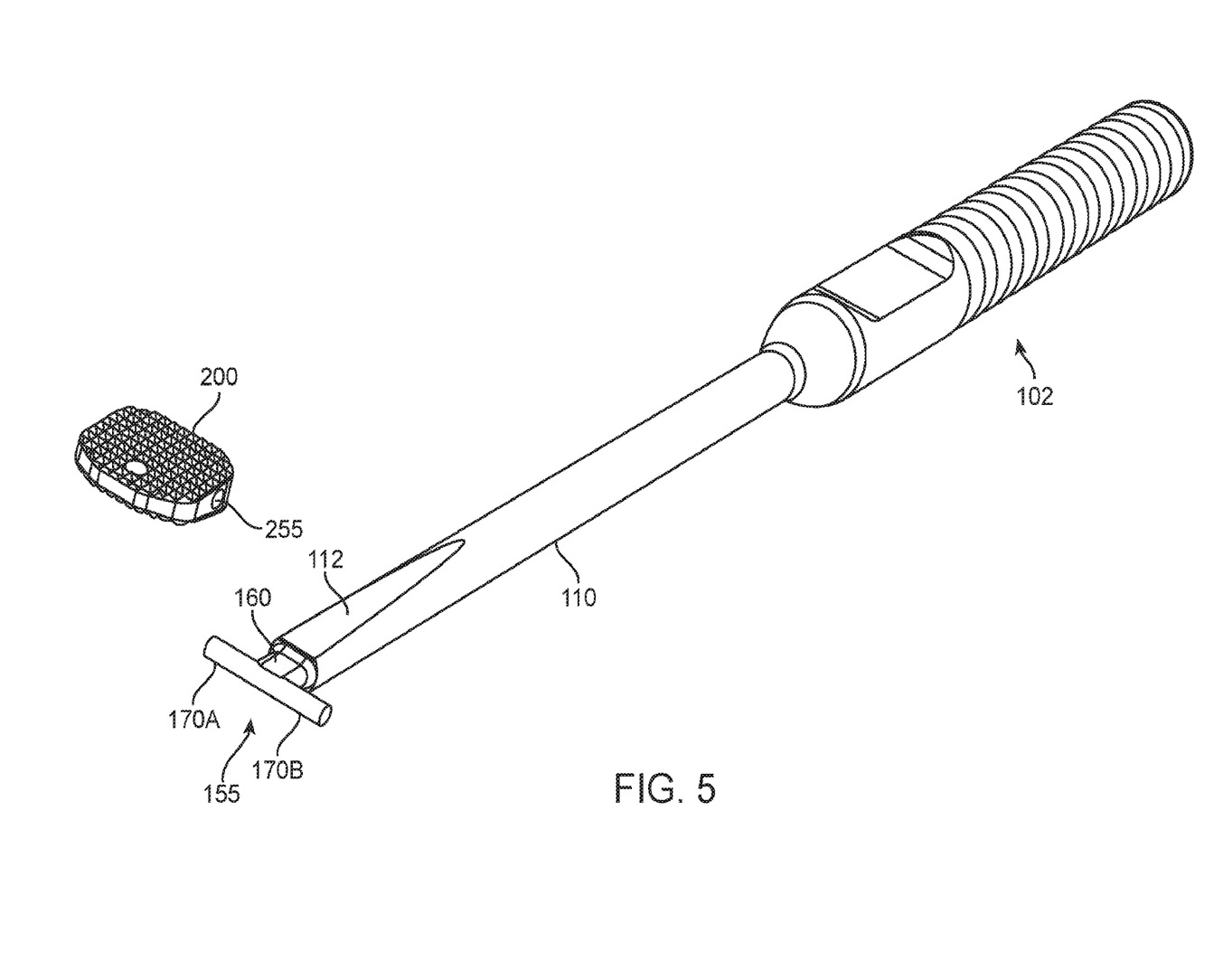
FIG. 5 is a component view of hybrid rasp tool.
Figure 6:
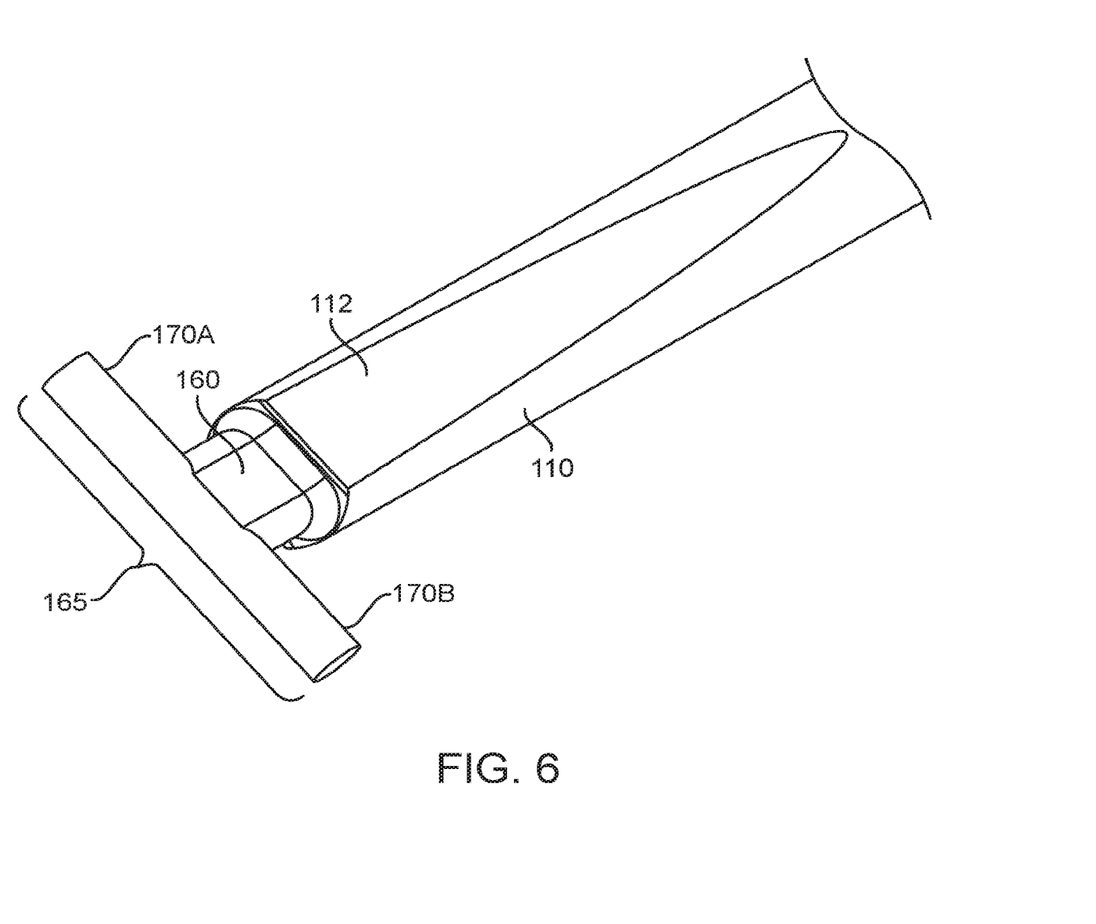
FIG. 6 is a partial view of the plastic connection neck of a hybrid rasp tool.

Shown in FIGS. 4-6 are aspects of the rasp head attachment. The rasp head 200 is fixed permanently at the proximal end 155 of the body. The material selected to form the body 100 should be configured to provide a predetermined amount of rigidity or flex along its axial length to balance the intended use, which may include the body bending a predetermined amount with the need to support the rasp head 200 for its intended use of resection. During resection the rasp head should have limited displacement off axis from the body and that limit of displacement may be the result of material choices.

The body material will also form the neck region 160 collar 165 and collar ends 170A and 170B of the body component. Shown in FIGS. 5 and 6 are the neck and arms. FIG. 4 shows a cut a-away view of an assembled hybrid rasp device wherein the placement of the neck 160, collar 165 and collar ends 170A/170B relative to the rasp head are shown.

The rasp head 200 is configured to resect bone or tissue at a surgical site. Accordingly, the rasp head should be constructed of a material of sufficient hardness to accomplish same. Moreover because the rasp head can be co-molded with the body, it needs to withstand the pressure, thermal changes associated with injection molding. By co-molding the rasp head to the body a compact rasp tool is constructed eliminating catches and latches to connect a rasp head to a support member.

Although the rasp head shown in FIG. 5 is illustrated as a single piece the rasp head may be formed of two or more parts combined together prior to co-molding. In some instances the rasp head will be a ceramic or metallic material. One opening 255 to the lateral passageway is also shown.

Figure 7:
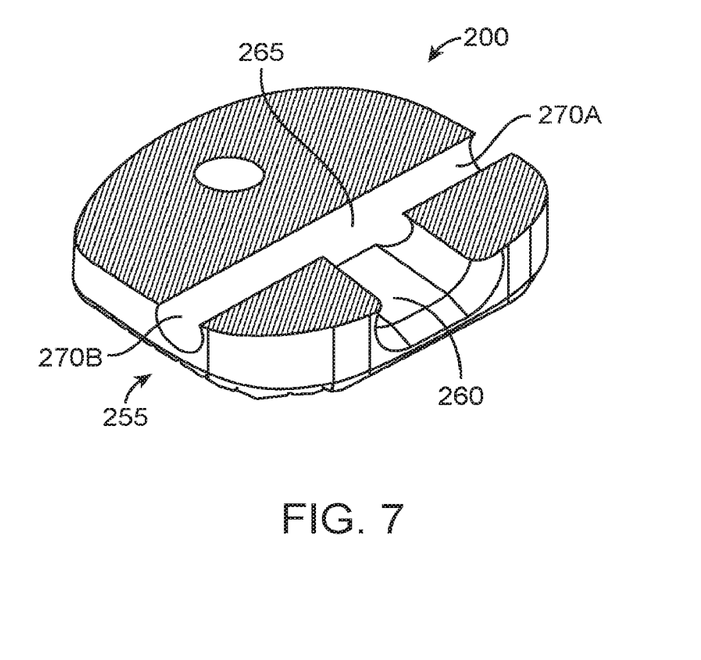
FIG. 7 is a cutaway view of the rasp head shown in FIG. 3A.

FIG. 7 illustrates a cut-away view of the rasp head. A fluid connection 260 oriented axially to the body is formed into the rasp head. The fluid connection 260 intersects with and is fluidly connected to lateral passageway 265 which run perpendicular to the body. The lateral passageway 265 has a first side 270A and a second side 270B formed respectively on either side of the fluid connection 260. The fluid connection and the lateral passageway together form a cavity through the rasp head by which the injection molded material will pass during production of the device. The lateral passageway is configured to allow the injection material to flow through.

Figure 8:
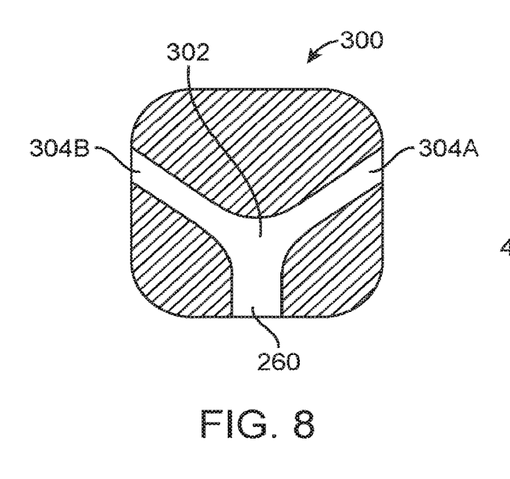
FIGS. 8-11 show aspects of fluid connections within the rasp head.
Figure 9:
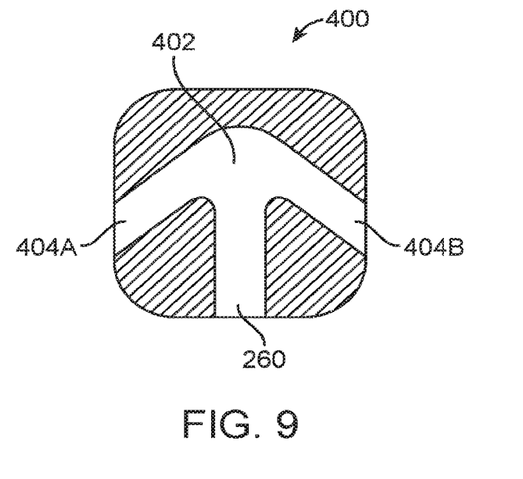
Figure 10:
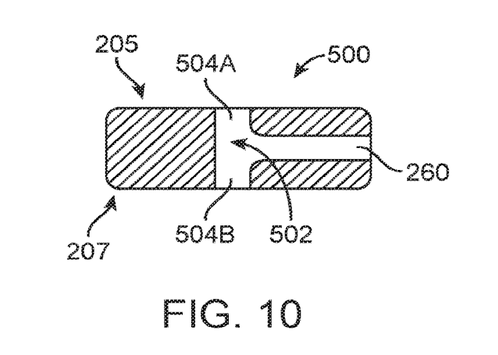
Figure 11:
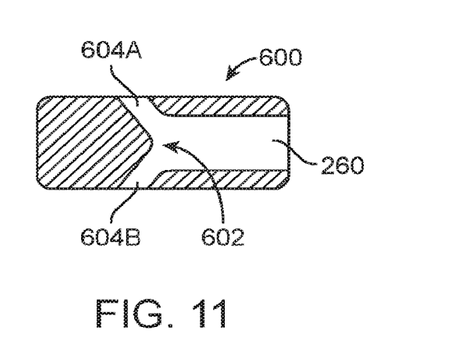

FIG. 8 shows a sectional top view of a rasp head 300 with a "Y" shaped channel having a fluid passageway 302 with sides 304A and 304B at oblique angles from the fluid connection 260. FIG. 9 shows a sectional top view of a rasp head 400 with an arrow shaped channel having a fluid passageway 402 with sides 404A and 404B at acute angles from the fluid connection 260. FIG. 10 shows a cross sectional view of a rasp head 500 with a "T" shaped channel with sides 504A and 504B orthogonal to the shaft and fluid passageway 302 spanning from the top side 205 to the bottom side 207 of the rasp head. FIG. 11 shows a cross sectional view of a rasp head 600 with a "Y" shaped channel with sides 504A and 504B orthogonal to the shaft and fluid passageway 302 spanning from the top side 205 to the bottom side 207 of the rasp head.

Figure 12:
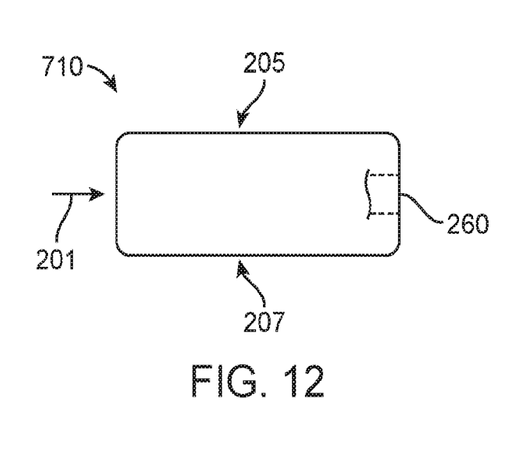
FIGS. 12-14 show aspects of rasp head cross sections.
Figure 13:
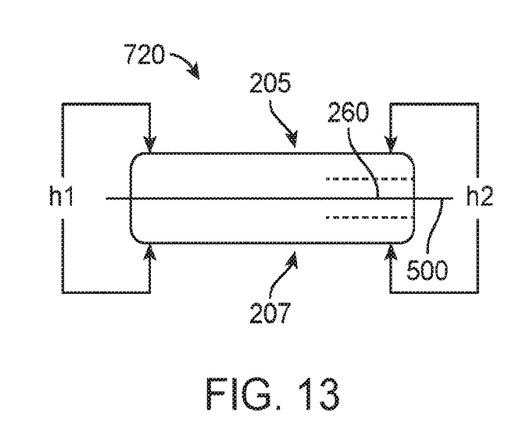
Figure 14:
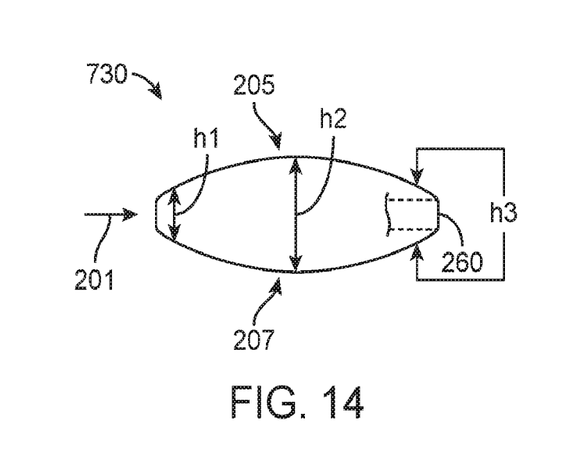

FIGS. 12 through 14 show side views of several rasp heads. FIG. 12 shows a side view of rasp head 710 with parallel sides 205 and 207. FIG. 13 shows a side view of a rasp head 720 showing an axis of the rasp head 500 which is parallel or flat to the bottom side 207 and a top side 205 that is tapered relative to the axis of the rasp head. FIG. 14 shows a side view of rasp head 730 which has a complex shape shown as a convex top side 205 and a convex bottom side 207. In this implementation the center of the rasp head is at height two "h2." Height one "h1" corresponds to the distance between the concave top side 205 and the concave bottom side 207. Height three "h3" corresponds to the height of the fluid connection 260. The skilled artisan and those of ordinary skill in the art will recognize that FIG. 14 may be convex or concave on one side and flat on another side.

Figure 15:
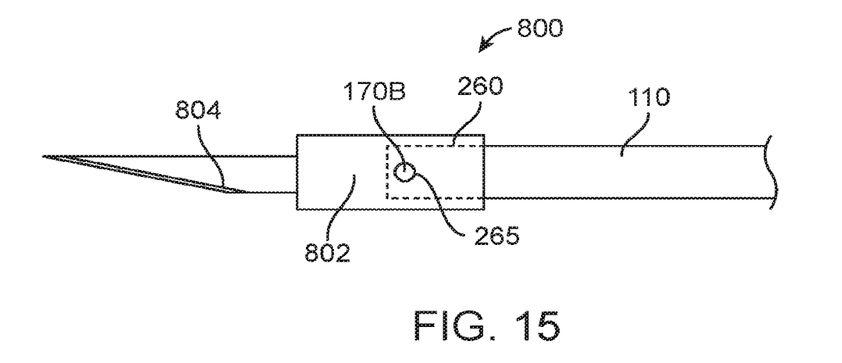
FIGS. 15-17 show cutting tools co-molded with a handle.

FIG. 15 illustrates a disposable cutting device 800 with a plastic shaft 110 co-molded to a support collar 802 affixed to a blade 804. Collar end 170B can be seen through lateral passageway 265 which is fluidly connected to fluid connection 260 oriented axially to the shaft and collar.

Figure 16:
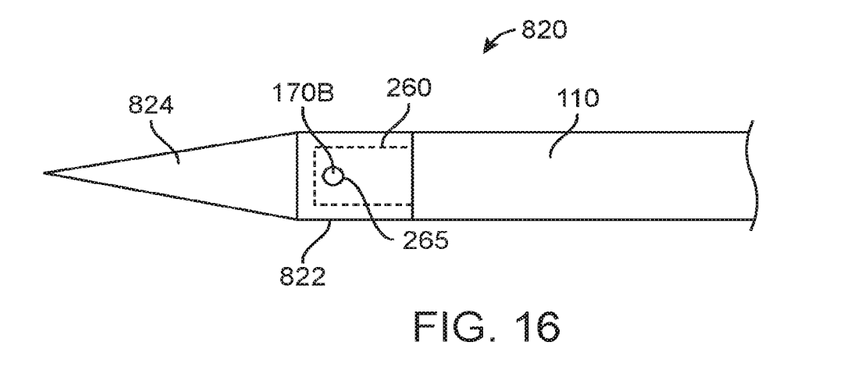

FIG. 16 illustrates a disposable cutting device 820 with a plastic shaft 110 co-molded to a support collar 822 affixed to a drill 824. Collar end 170B can be seen through lateral passageway 265 which is fluidly connected to fluid connection 260 oriented axially to the shaft and collar.

Figure 17:
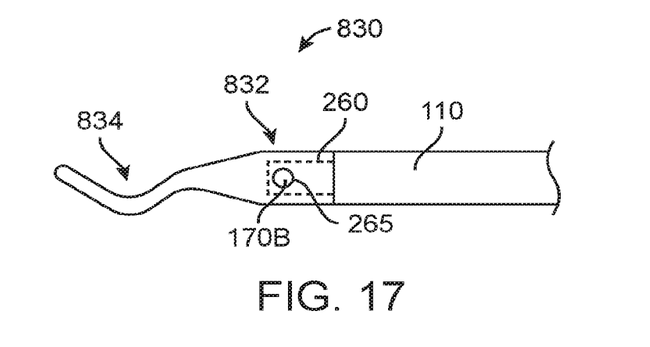

FIG. 17 illustrates a disposable scraping device 830 with a plastic shaft 110 co-molded to a support collar 832 affixed to or formed as part of a scraper 834. Collar end 170B can be seen through lateral passageway 265 which is fluidly connected to fluid connection 260 oriented axially to the shaft.

Those of ordinary skill in the art will recognize that the scope of the disclosure includes nonlinear lateral passageways and lateral passageways which may have additional branches. The lateral passageway is configured to retain injection material in a fashion that fixes the rasp head to the body and prevents rotation of the rasp head on the body within the parameters of intended usage.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A disposable cutting tool comprising:
   an elongated molded body with a proximal end and a distal end;
   a handle portion formed near the distal end and a support shaft formed near the proximal end; and,
   the support shaft affixed to a rasp head having a height, a top side and a bottom side via portions of the body co-molded into a fluid connection within the rasp head.

2. The tool of claim 1 further comprising at least one of divots, bumps and generally flat regions on the handle portion.

3. The tool of claim 1 further comprising a molded neck region extending from said body and formed within said fluid connection.

4. The tool of claim 3 further comprising a passageway in said rasp head;
   a third side and a fourth side in said rasp head fluidly connected to said passageway; and
   a molded collar region connected to said molded neck region and formed within said passageway, wherein said molded collar region extends into said third side and said fourth side.

5. The tool of claim 4 wherein said passageway is orthogonal and perpendicular to said shaft, the passageway extending from said top side to said bottom side of said rasp head.

6. The tool of claim 4 wherein said passageway is at an acute angle to said shaft.

7. The tool of claim 4 wherein said passageway is at an oblique angle to said shaft.

8. The tool of claim 4 wherein said passageway is "Y" shaped extending from said top side to said bottom side of said rasp head.

9. The tool of claim 1 wherein at least one of said rasp head and said support shaft are tapered.

10. The tool of claim 1 wherein at least one of said top side and bottom side of said rasp head is parallel to the axis of said rasp head and the other side is angled relative to the axis of said rasp head.

11. The tool of claim 9 wherein said rasp head tapers from a first height "h1" at its proximal end to a second height "h2" at its distal end.

12. The tool of claim 9 wherein said rasp head tapers from a first height "h1" at its proximal end to a second height "h2" at its mid-section and to a third height "h3" at its distal end.

13. The tool of claim 9 wherein said shaft tapers from a first cross sectional height "sh1" to a second cross sectional height "sh2" and the second cross sectional height is generally the same as a second height "h2".

14. The tool of claim 1 wherein said rasp head is configured to be replaceable by one of a drill, scalpel and scraper.

15. An ergonomic disposable rasp tool comprising:
an elongated molded body with a proximal end and a distal end;
a handle portion formed near the distal end and a support shaft formed near the proximal end; and
non-circular regions in cross section on said handle portion;
wherein said support shaft is affixed to a rasp head having a height, a top side and a bottom side via portions of said body co-molded into a fluid connection within said rasp head; and,
wherein said non-circular regions provide preselected gripping surfaces on said handle.

16. The ergonomic disposable rasp tool of claim 15 wherein said non-circular regions are at least one of divots, bumps and generally flat regions.

17. The tool of claim 15 further comprising a molded neck region extending from said body and formed within said fluid connection.

18. The tool of claim 17 further comprising:
a passageway in the rasp head;
a molded collar region connected to the neck region and formed within the passageway in the rasp head; and which extends into sides fluidly connected to the passageway.

19. A method of attaching a rasp head, the method comprising:
forming a metal rasp head having a fluid pathway therethrough;
molding an elongated body with support shaft co-molded into the rasp head via said fluid pathway; the fluid pathway having one or more branches into one or more sides.

20. The method of claim 19 wherein said one or more branches are perpendicular to said support shaft.

21. The method of claim 19 wherein said one or more branches are formed at one of an acute and oblique angle to said shaft.

* * * * *